US012667531B2

(12) United States Patent
Hippe et al.

(10) Patent No.: US 12,667,531 B2
(45) Date of Patent: Jun. 30, 2026

(54) AGENT FOR OXIDATIVELY DYEING KERATIN FIBERS, CONTAINING AT LEAST ONE OXIDATION DYE PRECURSOR OF THE DEVELOPER TYPE AND ISATIN

(71) Applicant: Henkel AG & Co. KGaA, Duesseldorf (DE)

(72) Inventors: Thomas Hippe, Appen (DE); Astrid Kleen, Haseldorf (DE); Hartmut Manneck, Barnitz (DE); Stefan Hoepfner, Hamburg (DE); Tugce Cansev, Hamburg (DE)

(73) Assignee: Henkel AG & Co. KGaA, Düsseldorf (DE)

( * ) Notice: Subject to any disclaimer, the term of this patent is extended or adjusted under 35 U.S.C. 154(b) by 0 days.

(21) Appl. No.: 18/887,544

(22) Filed: Sep. 17, 2024

(65) Prior Publication Data

US 2025/0025399 A1 Jan. 23, 2025

Related U.S. Application Data

(63) Continuation of application No. PCT/EP2023/050085, filed on Jan. 3, 2023.

(30) Foreign Application Priority Data

Mar. 21, 2022 (DE) ......................... 102022202760.4

(51) Int. Cl.

| | |
|---|---|
| ***A61Q 5/10*** | (2006.01) |
| ***A61K 8/19*** | (2006.01) |
| ***A61K 8/41*** | (2006.01) |
| ***A61K 8/46*** | (2006.01) |
| ***A61K 8/49*** | (2006.01) |

(52) U.S. Cl.

CPC ................ *A61K 8/492* (2013.01); *A61K 8/19* (2013.01); *A61K 8/411* (2013.01); *A61K 8/415* (2013.01); *A61K 8/418* (2013.01); *A61K 8/466* (2013.01); *A61K 8/4926* (2013.01); *A61Q 5/10* (2013.01); *A61K 2800/882* (2013.01)

(58) Field of Classification Search

CPC .......... A61K 8/492; A61K 8/19; A61K 8/411; A61K 8/415; A61K 8/418; A61K 8/466; A61K 8/4926; A61K 2800/882; A61K 8/41; A61K 8/4946; A61K 2800/30; A61K 2800/42; A61K 2800/4324; A61K 2800/88; A61K 8/34; A61K 8/44; A61Q 5/10

USPC ...................................................... 8/405, 406

See application file for complete search history.

(56) References Cited

U.S. PATENT DOCUMENTS

| | | | | |
|---|---|---|---|---|
| 4,750,908 A * | 6/1988 | Rosenbaum | A61Q 5/065 | 8/405 |
| 5,261,926 A * | 11/1993 | Lang | A61K 8/492 | 8/408 |
| 6,203,579 B1 * | 3/2001 | Moeller | A61Q 5/10 | 8/405 |

FOREIGN PATENT DOCUMENTS

| | | | | |
|---|---|---|---|---|
| DE | 2716671 A1 | 10/1978 | | |
| DE | 102008056811 A1 | 9/2009 | | |
| EP | 2559456 A2 | 10/2013 | | |
| EP | 3943161 A1 | 1/2022 | | |
| KR | 20060073522 A * | 6/2006 | | A61Q 5/10 |
| WO | 9847472 A1 | 10/1998 | | |

OTHER PUBLICATIONS

Anonymous: "Description of a Proposed Reference Dose Resorcinol", r Sep. 1, 2004 (Sep. 1, 2004), XP055300873, Gefunden im Internet: URL:http://www.dep.state.pa.us/dep/sub ject /advcoun/cleanup/2004/Dec8/AMEC_Resorcinol RFD_090804.pdf [gefunden am Sep. 8, 2016] Executive summary, ES-2 Hazard Identification, 3. Use of resorcinol, 5. Hazard Identification, 5.1. Human.

PCT International Search Report—WO PCT/EP2023/050085—Completed: Apr. 14, 2023 Mailing date: Apr. 24, 2023—Number of pages: 149.

* cited by examiner

*Primary Examiner* — Eisa B Elhilo

(74) *Attorney, Agent, or Firm* — Blank Rome LLP

(57) ABSTRACT

The present invention relates to an agent for oxidatively dyeing keratin fibers, and in particular human hair, containing, in a cosmetic carrier, (a) at least one oxidation dye precursor of the developer type, and (b) isatin, and (c) at least one alkalizing agent from the group consisting of ammonia, monoethanolamine, 2-amino-2-methylpropanol, arginine, lysine, ornithine, and histidine.

15 Claims, No Drawings

AGENT FOR OXIDATIVELY DYEING KERATIN FIBERS, CONTAINING AT LEAST ONE OXIDATION DYE PRECURSOR OF THE DEVELOPER TYPE AND ISATIN

FIELD OF INVENTION

The present invention relates to cosmetic agents for oxidatively dyeing keratin fibers and containing at least one oxidation dye precursor of developer type (a), isatin (b), and at least one alkalizing agent (c) from the group consisting of ammonia, monoethanolamine, 2-amino-2-methylpropanol, arginine, lysine, ornithine, and histidine.

A further subject matter is a multicomponent packaging unit (kit-of-parts) comprising two agents packaged separately in two containers, wherein the agent in the first container contains the ingredients (a), (b), and (c), and the agent in the second container contains at least one oxidizing agent from the group consisting of hydrogen peroxide and its addition products to organic or inorganic compounds.

A further subject matter is a method for the oxidative dyeing of keratin fibers, in which a previously described agent is applied to the keratin fibers and rinsed out again after an exposure time.

BACKGROUND

In order to provide a color-changing cosmetic agent—in particular, for keratinous fibers—such as hair, a person skilled in the art is aware of various dyeing systems depending upon the coloration requirement. For permanent, intense colorations having appropriate fastness properties, so-called oxidation dyes are used. Such dyes typically contain oxidation dye precursors, known as developer components, and coupler components, which together form the actual dyes under the influence of oxidizing agents—for example, hydrogen peroxide. Oxidative dyeing agents are characterized by outstanding, long-lasting coloring results.

The oxidation dye precursors (developers and couplers) themselves are not colored, but, rather, the actual dyes are formed only during the course of the application when the oxidation dye precursors come into contact with the oxidizing agent (hydrogen peroxide). In a chemical reaction, the developers used as oxidation dye precursors (such as p-phenylene diamine or its derivatives) are first oxidatively converted by hydrogen peroxide into a reactive intermediate, also called quinonimine or quinone diimine, which then reacts in an oxidative coupling reaction with the couplers to form the corresponding dye.

With oxidation dyes, hair can be dyed both in intensive mode shades and in natural shades by choosing the suitable developer components and coupler components. A large area of application for the oxidative dyeing agents is the coloring of gray hair in a natural shade, which resembles the hair color that the user had when they were younger. A person skilled in the art knows the use of developers based upon the base body of 1,4-diaminobenzene (para-phenylene diamine) and couplers with a resorcinol structure (1,3-dihydroxybenzene) as a classic combination for producing oxidative colorations in the brown to dark-blond range.

Said oxidation dyes have been used for decades. Although they are only intended for extracorporeal use on keratin fibers such as head hair, eyelashes, and eyebrows, contact of the dyeing agent with the scalp cannot be completely avoided during use. In order to ensure the highest possible product safety for customers, the commercially available oxidation dye precursors are continuously checked for their physiological tolerance—for example, by the Scientific Committee on Consumer Products (SCCP), an advisory body of the European Commission. It is known that some of the oxidation dye precursors, and in particular some of the oxidation bases of the para-phenylene diamine type, can have a certain potential for sensitization. In order to rule out allergic reactions during or after the dyeing process, the customer is therefore advised to perform a test with a small amount of the dye on the skin before using the dye on the hair. In addition to skin sensitization, other physiological effects are also monitored.

Resorcinol, 4-chlororesorcinol, and 2-methylresorcinol are common oxidation dye precursors with a 1,3-dihydroxybenzene base body. In its last opinion from March 2021, SCCP came to the conclusion that the use of resorcinol in oxidative hair dyes with a resorcinol concentration of up to 1.25 wt % in the ready-to-use mixture was considered safe. The SCCP stated that resorcinol has a thyroid-inhibiting effect. Although a definite level of exposure required for such an effect cannot be derived from the available studies in humans, most of these studies indicate a relatively much higher exposure than is the case in cosmetics.

SUMMARY OF THE INVENTION

In order to take into account the concerns of some consumers with regard to product safety, the object of the present invention was to provide an agent for oxidatively dyeing keratin fibers, and in particular human hair, with which a broad color spectrum can be covered—in particular, a natural color palette with cool natural shades and warm natural shades, and a gold color series which leads to colors having high fastness properties—without impairing product safety. In particular, dyeing in these natural shades should be possible without the use of couplers of the resorcinol type.

Many users dye their hair over decades in the same shade and do not want a sudden, obvious, visible change to their usual hair color. For these users, it is therefore essential to allow the customary, resorcinol-containing hair dye to be replaced by a new, resorcinol-free product without a shift in shade. A central challenge of the present application was therefore to find a new, resorcinol-free hair dye which, in its color effect and its color result, corresponds as precisely as possible to the resorcinol-containing dyeing agent used to date.

Surprisingly, it has now been found that this object can be excellently achieved by an oxidative dyeing agent containing an oxidation dye precursor of developer type (a), isatin (b), and at least one alkalizing agent (c) from the group consisting of ammonia, monoethanolamine, 2-amino-2-methylpropanol, arginine, lysine, ornithine, and histidine.

A first subject matter of the present invention is an agent for oxidatively dyeing keratinous fibers, and in particular human hair, containing, in a cosmetic carrier, (a) at least one developer-type oxidation dye precursor, and (b) isatin, and (c) at least one alkalizing agent from the group consisting of ammonia, monoethanolamine, 2-amino-2-methylpropanol, arginine, lysine, ornithine, and histidine.

The work leading to this invention has shown that the oxidative dyeing of hair using a developer (a) in combination with isatin (b) leads to very intense dyeing with excellent fastness properties if an alkalizing agent (c), selected from the group consisting of ammonia, monoethanolamine, 2-amino-2-methylpropanol, arginine, lysine, ornithine, and histidine, is still used in the dyeing agent.

DETAILED DESCRIPTION OF THE INVENTION

Keratin Fibers

Keratin fibers are, in principle, understood to mean all types of animal hair—for example, wool, horsehair, angora hair, furs, feathers, and products or textiles manufactured therefrom. Preferably, however, the keratin fibers are human hair.

Agents for Oxidative Dyeing

The term, "agent for oxidation dyeing," of keratin fibers used according to the invention is understood to mean oxidation dyes. Oxidative dyeing agents contain oxidation dye precursors, so-called developers, and coupler components. Developers and couplers diffuse separately into the keratin fibers and, in a chemical reaction with one another, form the actual dyes under the influence of an alkalizing agent (e.g., ammonia) and an oxidizing agent (hydrogen peroxide). Depending upon the quantity of oxidizing agent used, the keratin fibers are simultaneously lightened to a greater or lesser extent during coloring, since the oxidizing agent not only initiates the dye-forming process of the developers and couplers, but also oxidatively destroys the hair's own pigments (melanins). Depending upon the used amounts of the oxidation dye precursor products and of the oxidizing agent, the oxidative coloration can therefore be predominantly a coloration (with high dye proportion) or predominantly a lightening (with high proportion of oxidizing agent). In the latter case, the oxidation dye precursors are mostly used for shading the brightening result.

The agents according to the invention contain the components essential to the invention in each case in a cosmetic carrier, and preferably in a suitable aqueous, alcoholic, or aqueous-alcoholic carrier. For the purpose of hair coloring, such carriers are for example creams, emulsions, gels, or also surfactant-containing foaming solutions, such as for example shampoos, foam aerosols, foam formulations, or other preparations which are suitable for application to hair.

The oxidative dye described above is a ready-to-use dye which is applied in this form containing the components (a) and (b) and (c) for application to the keratin fibers.

Oxidation Dye Precursors of Developer Type (a)

Oxidative dyeing agents contain oxidation dye precursors, so-called developers, and coupler components, for the formation of the coloring. Developers and couplers diffuse separately into the keratin fibers and form the actual dyes in a chemical reaction with one another under the influence of ammonia as alkalizing agent and an oxidizing agent. Depending upon the quantity of oxidizing agent employed, the keratin fibers are simultaneously lightened to a greater or less extent during coloring, since the oxidizing agent not only initiates the dye-forming process of the developers and couplers, but also oxidatively destroys the hair's own pigments (melanins). Depending upon the used amounts of the oxidation dye precursor products and of the oxidizing agent, the oxidative color change can therefore be predominantly a coloration (with high dye proportion) or predominantly a lightening (with high proportion of oxidizing agent). In the latter case, the oxidation dye precursors are mostly used for shading the brightening result.

As a first essential component, the oxidative dyeing agents according to the invention contain at least one oxidation dye precursor of the developer type, also referred to as developer for short.

Particularly suitable oxidation dye precursors of the developer type are selected from the group consisting of p-toluylene diamine, 2-methoxymethyl-p-phenylene diamine, 2-(2-hydroxyethyl)-p-phenylene diamine, N,N-bis-(2-hydroxyethyl)-p-phenylene diamine, p-phenylene diamine, and the physiologically tolerated salts thereof.

In a particularly preferred embodiment, an agent according to the invention is therefore characterized in that it contains at least one oxidation dye precursor of the developer type (a) which is selected from the group of p-toluylene diamine, 2-methoxymethyl-p-phenylene diamine, 2-(2-hydroxyethyl)-p-phenylene diamine, N,N-bis-(2-hydroxyethyl)-p-phenylene diamine, p-phenylene diamine, and the physiologically tolerated salts thereof.

P-toluylene diamine is alternatively also referred to as 2,5-toluylene diamine, p-toluylene diamine (abbreviation: PTD), 2,5-diaminotoluene, 2-methyl-p-phenylene diamine or 2,5-diaminomethylbenzene. PTD has the CAS number 95-70-5.

2-methoxymethyl-p-phenylene diamine is alternatively also referred to as 2-methoxymethyl-1,4-benzene diamine and, in the form of its free base, bears the CAS number 337906-36-2.

2-(2-hydroxyethyl)-p-phenylene diamine is alternatively referred to as 2-(2,5-diaminophenyl) ethanol and, in the form of its free base, carries the CAS number 93841-24-8.

N,N-bis-(2-hydroxyethyl)-p-phenylene diamine in the form of its free base has the CAS number 7575-35-1.

With an oxidative dyeing agent, which contains a developer (a) of the aforementioned group with the base structure of the 1,4-diaminobenzene, hair was able to be colored with very high intensity in natural shades, and in particular in dark brown, medium brown, and dark blond shades. It was also particularly surprising that the hair could be colored in a shade which was particularly strongly similar to the shade obtained with a dyeing agent containing the classic combination of PDT and resorcinol.

The agents which contain at least one oxidation dye precursor of the developer type (a), which is selected from the group of p-toluylene diamine, 2-methoxymethyl-p-phenylene diamine, and the physiologically tolerated salts thereof, have proven to be very particularly suitable for achieving the object according to the invention.

In a particularly preferred embodiment, an agent according to the invention is therefore characterized in that it contains at least one oxidation dye precursor of the developer type (a) which is selected from the group of p-toluylene diamine, 2-methoxymethyl-p-phenylene diamine, and the physiologically tolerated salts thereof.

However, the agent according to the invention can also contain other developers (a) to form shades with a reddish natural tone. For example, developers from the group of 4-amino-3-methylphenol, p-aminophenol, 4,5-diamino-1-(2-hydroxyethyl)pyrazole, and their physiologically tolerated salts are particularly suitable for this purpose. These developers can be used either as a group on their own or also together with one or more developers having a basic structure of p-phenylene diamine.

In a further preferred embodiment, an agent according to the invention is therefore characterized in that it contains at least one oxidation dye precursor of developer type (a), which is selected from the group consisting of 4-amino-3-methylphenol, p-aminophenol, 4,5-diamino-1-(2-hydroxyethyl)pyrazole, and the physiologically tolerated salts thereof.

In a further very particularly preferred embodiment, an agent according to the invention is therefore characterized in that it comprises at least one oxidation dye precursor of the developer type (a), which is selected from the group consisting of p-toluylene diamine, 2-methoxymethyl-p-phenylene diamine, 2-(2-hydroxyethyl)-p-phenylene diamine, N,N-bis-(2-hydroxy-ethyl)-p-phenylene diamine, p-phenylene diamine, 4-amino-3-methylphenol, p-aminophenol, 4,5-diamino-1-(2-hydroxyethyl)pyrazole, and physiologically tolerated salts thereof.

The developers of the above-mentioned groups can be used in the agent according to the invention in the form of their free base or else in the form of their physiologically tolerated salts. A physiologically tolerated salt is understood to mean a salt of the developer that is well tolerated by the user under physiological conditions, i.e., during use of the agent. Physiologically tolerated salts are in particular the chlorides, bromides, sulfates, and hemisulfates of developers (a).

In a further particularly preferred embodiment, an agent according to the invention is therefore characterized in that it contains at least one oxidation dye precursor of developer type (a) which is selected from the group of p-toluylene diamine, p-toluylene diamine sulfate, p-toluylene diamine chloride, p-toluylene diamine bromide, 2-methoxymethyl-p-phenylene diamine, 2-methoxymethyl-p-phenylene diamine sulfate, 2-methoxymethyl-p-phenylene diamine chloride and 2-methoxymethyl-p phenyldiamine bromide, 4,5-diamino-1-(2-hydroxyethyl)pyrazole chloride, 4,5-diamino-1-(2-hydroxyethyl)-pyrazole bromide, and 4,5-diamino-1-(2-hydroxyethyl)pyrazole sulfate.

Depending upon the desired color effect, it can furthermore be preferred for the agent to additionally contain one or more further oxidation dye precursors of the developer type, which are selected from the group of bis-(2-hydroxy-5-aminophenyl)methane, 1,3-bis-(2,5-diaminophenoxy)propane-2-ol, N,N'-bis-(4-aminophenyl)-1,4-diazacycloheptane, 1,10-bis-(2,5-diaminophenyl)-1,4,7,10-tetraoxadecane, 4-amino-3-methylphenol, 4-amino-2-aminomethylphenol, 4-amino-2-(1,2-dihydroxyethyl)phenol, 4-amino-2-(diethylaminomethyl)phenol, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one, and the physiologically tolerated salts thereof.

The developers(s) are preferably used in specific quantity ranges in the agent according to the invention. The agent preferably contains, relative to the total weight of the agent, one or more oxidation dye precursors of developer type (a) in a total amount of 0.001 to 10.0 wt %, preferably 0.01 to 6.0 wt %, more preferably 0.1 to 5.0 wt %, and very particularly preferably 0.15 to 4.7 wt %.

In a particularly preferred embodiment, an agent according to the invention is thus characterized in that the agent contains, relative to the total weight of the agent, one or more oxidation dye precursors of developer type (a) in a total amount of 0.001 to 10.0 wt %, preferably 0.01 to 6.0 wt %, more preferably 0.1 to 5.0 wt %, and very particularly preferably 0.15 to 4.7 wt %.

Isatin

As a second component substantial to the invention, the oxidation dye is isatin (b). Isatin is the compound of formula (ISA), which can alternatively also be referred to as 2,3-indoline-dione or as 2,3-dioxoindoline (ISA)

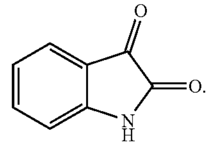

Isatin has the CAS number 91-56-5.

With regard to an optimal achievement of the object according to the invention, isatin (b) is preferably contained in specific quantity ranges in the agent according to the invention. Particularly good results were obtained when the agent contained, relative to the total weight of the agent, 0.001 to 10 wt %, preferably 0.01 to 5 wt %, more preferably 0.1 to 3.5 wt %, and very particularly preferably 0.15 to 2.5 wt % isatin (b).

In a particularly preferred embodiment, an agent according to the invention is thus characterized in that it contains, relative to the total weight of the agent, 0.001 to 10 wt %, preferably 0.01 to 5 wt %, more preferably 0.1 to 3.5 wt %, and particularly preferably 0.15 to 2.5 wt % isatin (b).

Isatin is commercially available from different suppliers, such as Acros, Sigma Aldrich, Thermo Scientific, etc.

Weight Ratio of Developers (a) to Isatin (b) on Average

The shade resulting from the coloration on the hair depends both upon the amounts of developer(s) (a) used and upon the amount of the isatins (b) contained in the agent. As is known from typical dyeing practice, the higher the amounts of developers (a) and isatin (b) used, the higher the intensity of the coloration. However, the nature of the resulting coloring can be controlled by the quantitative ratio in which the developers of group (a) and isatin (b) are used in the oxidative dye.

The colors produced on the hair then had a particularly high similarity to the colorations obtained with the couplers of the resorcinol type if the agent contained the developers (a) and isatin (b) in a weight ratio which has a value of 2:1 to 1:2, preferably 1.9:1 to 1:1, more preferably 1.9:1 to 1.1:1, even more preferably 1.8:1 to 1.1:1, and very particularly preferably 1.7:1 to 1.2:1. This effect was observed in particular in the darker natural shades, such as dark brown and medium blond.

In a particularly preferred embodiment, an agent according to the invention is thus characterized in that the weight ratio of all the developers of the group (a) contained in the agent to the isatin (b) contained in the agent, i.e., the weight ratio (a)/(b), has a value of 2:1 to 1:2, preferably 1.9:1 to 1:1, more preferably 1.9:1 to 1.1:1, even more preferably 1.8:1 to 1.1:1, and very particularly preferably 1.7:1 to 1.2:1.

In the preferred weight ratio (a)/(b) of 1.9:1 to 1:1, for example, the developer (a) or developers (a) is/are used in the agent either in the same amount as isatin (b) or in an up to 1.9-fold weight excess. Very particularly preferably, in comparison with the isatin (b), the developers (a) are used in a 1.2-fold to 1.7-fold weight excess.

Alkalizing Agent

Coloring processes on keratin fibers typically take place in an alkaline environment. To protect the keratin fibers as well as the skin as much as possible, however, it is not desirable to adjust to too high a pH value. It is therefore preferred if the pH of the ready-to-use agent is between 6 and 11, and in particular between 7 and 10.5. The pH values in the sense of the present invention are pH values which have been measured at a temperature of 22° C.

The work leading to this invention has shown that good color results were obtained in particular if an alkalizing agent from the group consisting of ammonia, monoethanolamine, 2-amino-2-methylpropanol, arginine, lysine, ornithine, and histidine was used in the dyeing agent according to the invention. For this reason, the dyeing agent according to the invention contains as a third substantial ingredient at least one alkalizing agent (c) selected from the group consisting of ammonia, monoethanolamine, 2-amino-2-methylpropanol, arginine, lysine, ornithine, and histidine.

Within this group, the best results were obtained with ammonia and monoethanolamine. For this reason, the agents containing at least one alkalizing agent (c) from the group consisting of ammonia and monoethanolamine, and very particularly preferably ammonia, are particularly preferred. Ammonia is most preferred.

In a particularly preferred embodiment, an agent according to the invention is therefore characterized in that it contains at least one alkalizing agent (c) from the group consisting of ammonia and monoethanolamine, and very particularly preferably ammonia.

By using the suitable or preferred alkalizing agent, the pH value suitable for the oxidation dyeing process can be configured in the dyeing agent according to the invention, which is in the range of 6.5 to 11.5, preferably 8.5 to 11.0, and very particularly preferably 9.0 to 10.5.

In the context of a further preferred embodiment, an agent according to the invention is characterized in that it contains water and has a pH in the range of 6.5 to 11.5, preferably 8.5 to 11.0, and very particularly preferably 9.0 to 10.5.

For precise adjustment of the pH, the dyeing agent can also contain one or more acidifying agents in addition to the alkalizing agents (c). According to the invention, preferred acidifying agents are food acids, such as citric acid, acetic acid, malic acid, or tartaric acid, as well as diluted mineral acids. The pH values in the sense of the present invention are pH values which have been measured at a temperature of 22° C.

Further Couplers (d) in Oxidation Dyes

For precise shading and/or fine adjustment of the desired color shade, the oxidative dye can also contain further couplers (d) in addition to the oxidation dye precursor(s) of the developer type (a) and isatin (b).

Further very well-suited couplers can be selected for example from the group consisting of 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylene diamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethyl)-1-methylbenzene, 1-amino-3-bis (2-hydroxyethyl)aminobenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, or mixtures of said compounds or the physiologically tolerated salts thereof.

In a particularly preferred embodiment, an agent according to the invention is thus characterized in that it contains at least one oxidation dye precursor of the coupler type (d) which is selected from the group of 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylene diamine, 2(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethyl)-1-methylbenzene, 1-amino-3-bis-(2-hydroxyethyl)aminobenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, or mixtures of said compounds or the physiologically tolerated salts thereof.

Particularly natural shades with great similarity to the corresponding resorcinol-containing dyes could be obtained if the dye additionally contained one or more couplers (d) which were selected from the group consisting of 3-aminophenol, 5-amino-2-methylphenol, 3-amino-2-chloro-6-methylphenol, 2-amino-3-hydroxypyridine, 1-methoxy-2-amino-4-(2-hydroxyethylamino)benzene, 6-hydroxyindole, or mixtures of these compounds or the physiologically tolerated salts thereof. For this reason, the use of couplers (d) from this group is explicitly very particularly preferred.

In an explicitly very particularly preferred embodiment, an agent according to the invention is therefore characterized in that it contains at least one oxidation dye precursor of coupler type (d) which is selected from the group consisting of 3-aminophenol, 5-amino-2-methylphenol, 3-amino-2-chloro-6-methylphenol, 2-amino-3-hydroxypyridine, 1-methoxy-2-amino-4-(2-hydroxyethyl amino)benzene, 6-hydroxyindole, or mixtures of said compounds or the physiologically tolerated salts thereof.

The couplers from the above-described group (d) are preferably used in specific quantity ranges in the agent according to the invention. Particularly positive results were obtained when the agent contained, relative to the total weight of the agent, one or more oxidation dye precursors of the coupler type (d) in a total amount of 0.001 to 10 wt %, preferably 0.01 to 5 wt %, more preferably 0.1 to 3.5 wt %, and very particularly preferably 0.15 to 2.5 wt %.

In a further preferred embodiment, an agent according to the invention is characterized in that the agent contains, relative to the total weight of the agent, one or more oxidation dye precursors of the coupler type (d) in a total amount of 0.001 to 10 wt %, preferably 0.01 to 5 wt %, more preferably 0.1 to 3.5 wt %, and very particularly preferably 0.15 to 2.5 wt %.

Dispensing with Resorcinol-Type Couplers

As already described above, with the agent of the present application, intense colorations in the natural tone range should be developed, which reproduce the shades that are produced with resorcinol-containing dyes as well as possible, without being dependent upon the use of couplers of the resorcinol type.

Resorcinol-type couplers or couplers from the group of resorcinols are understood to mean 1,3-dihydroxybenzene and its derivatives. Derivatives of 1,3-dihydroxybenzene are all compounds which have a 1,3-dihydroxybenzene basic structure and carry further substituents, but both hydroxyl groups of the 1,3-dihydroxybenzene must still be present.

The couplers from the group of resorcinols used as standard in market products are resorcinol, 2-methylresorcinol, and 4-chlororesorcinol. Couplers from the group of resorcinols are therefore understood in particular to be resorcinol, 2-methylresorcinol, and 4-chlororesorcinol. In the agent of the present application, these couplers are to be dispensed with, and therefore it is preferred if the total amount of precursors of the coupler type contained in the agent from the group of resorcinols, and in particular from the group consisting of resorcinol, 2-methylresorcinol, and 4-chlororesorcinol, is below 0.1 wt %, preferably below 0.05 wt %, particularly preferably below 0.01 wt %, and very particularly preferably 0 wt %.

In a further very particularly preferred embodiment, an agent according to the invention is therefore characterized in that, relative to the total weight of the agent, the total amount of the oxidation dye precursors of the coupler type contained in the agent from the group of resorcinols, and in particular from the group consisting of resorcinol, 2-methylresorcinol, and 4-chlororesorcinol, is below 0.1 wt %, preferably below 0.05 wt %, particularly preferably below 0.01 wt %, and very particularly preferably 0 wt %.

Direct Dyes

Furthermore, the agent according to the invention can optionally contain at least one direct dye. These are dyes which are drawn directly onto the hair and which do not require an oxidative process in order to form the color. Direct dyes are typically nitrophenylene diamines, nitroaminophenols, azo dyes, anthraquinones, triarylmethane dyes, or indophenols.

The direct dyes are each used preferably in an amount of 0.001 to 20 wt %, and in particular 0.05 to 5 wt %, in each case relative to the total preparation for use. The total quantity of direct dyes is preferably at most 3 wt %.

Direct dyes can be divided into anionic, cationic, and non-ionic direct dyes, which are selected and used by a person skilled in the art according to the requirements of the support base.

Preferred anionic direct dyes are the compounds known under the international names or trade names, Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, and Acid Black 52.

Preferred cationic direct dyes are Basic Blue 7, Basic Blue 26, Basic Violet 2 and Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Yellow 87, Basic Orange 31, and Basic Red 51.

In particular, non-ionic nitro dyes and quinone dyes and neutral azo dyes are suitable as non-ionic direct dyes. Preferred non-ionic direct dyes are the compounds known under the international names or trade names, HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, and 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid, and 2-chloro-6-ethylamino-4-nitrophenol.

Hydrogen Peroxide (e)

For the formation of the colors in the oxidation dyeing process, the oxidative dyeing agent according to the invention preferably contains at least one oxidizing agent (e) which is particularly preferably hydrogen peroxide and/or the addition products of hydrogen peroxide to organic or inorganic compounds.

In a preferred embodiment, hydrogen peroxide itself is used as an aqueous solution in the oxidation dye. The concentration of a hydrogen peroxide solution is determined by the legal requirements, on the one hand, and by the desired effect, on the other; preferably, 6 to 12 wt % solutions in water are used. Oxidative preferred according to the invention are characterized in that they contain 0.5 to 20 wt %, preferably 1 to 12.5 wt %, more preferably 2.5 to 10 wt %, and particularly preferably 3 to 8 wt % hydrogen peroxide, in each case relative to the total weight of the oxidative dyeing agent.

In a further particularly preferred embodiment, an agent according to the invention is therefore characterized in that it contains at least one oxidizing agent (e) from the group consisting of hydrogen peroxide and its addition products to organic or inorganic compounds.

In a particularly preferred embodiment, an agent according to the invention is characterized in that it contains, relative to the total weight of the agent, 0.5 to 20 wt %, preferably 1 to 12.5 wt %, more preferably 2.5 to 10 wt %, and particularly preferably 3 to 8 wt % hydrogen peroxide (e).

Additional Ingredients in the Agent

Preferably, an emulsifier or a surfactant is also added to the oxidative dyeing agents, wherein surface-active substances are referred to as surfactants or emulsifiers depending upon the field of application and are selected from anionic, cationic, zwitterionic, amphoteric, and non-ionic surfactants and emulsifiers.

In a further very particularly preferred embodiment, an agent according to the invention is therefore characterized in that it contains at least one surfactant selected from the group consisting of anionic, amphoteric, zwitterionic, and non-ionic surfactants.

Suitable anionic surfactants in agents according to the invention are all anionic surface-active substances suitable for use on the human body. These are characterized by a water-solubilizing, anionic group, such as for example a carboxylate, sulfate, sulfonate, or phosphate group, and a lipophilic alkyl group having about 8 to 30 carbon atoms. In addition, glycol ether or polyglycol ether groups, ester, ether, and amide groups, and hydroxyl groups can be contained in the molecule. Examples of suitable anionic surfactants are, in each case in the form of the sodium, potassium, and ammonium and mono-, di-, and trialkanol ammonium salts having 2 to 4 carbon atoms in the alkanol group,

- linear and branched fatty acids having 8 to 30 C atoms (soaps);
- ether carboxylic acids of the formula $RO(CH_2CH_2O)_x CH_2COOH$, in which R is a linear alkyl group having 8 to 30 C atoms, and x=0 or 1 to 16;
- acyl sarcosides having 8 to 24 C atoms in the acyl group;
- acyl taurides having 8 to 24 C atoms in the acyl group;
- acyl isethionates having 8 to 24 C atoms in the acyl group;
- sulfosuccinic acid mono- and dialkyl esters having 8 to 24 C atoms in the alkyl group and sulfosuccinic acid monoalkyl polyoxyethyl esters having 8 to 24 C atoms in the alkyl group and 1 to 6 oxyethyl groups;

linear alkane sulfonates having 8 to 24 C atoms;

linear α-olefin sulfonates having 8 to 24 C atoms;

sulfonates of unsaturated fatty acids having 8 to 24 C atoms and 1 to 6 double bonds;

α-sulfo fatty acid methyl esters of fatty acids having 8 to 30 C atoms;

alkyl sulfates and alkyl ether sulfates of the formula $RO(CH_2CH_2O)_xSO_3H$, in which R is a preferably linear alkyl group having 8 to 30 C atoms, and x=0 or 1 to 12;

mixtures of surface-active hydroxy sulfonates;

sulfated hydroxyalkyl polyethylene and/or hydroxyalkylene propylene glycol ethers;

esters of tartaric acid and citric acid with alcohols, which represent addition products of about 2-15 molecules ethylene oxide and/or propylene oxide to fatty alcohols having 8 to 22 C atoms;

alkyl and/or alkenyl ether phosphates of the formula

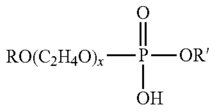

in which R preferably represents an aliphatic, optionally unsaturated hydrocarbon functional group having 8 to 30 carbon atoms, R' represents hydrogen, a functional group $(CH_2CH_2O)_yR$, and x and y independently of one another represent a number from 1 to 10;

sulfated fatty acid alkylene glycol esters of the formula $RC(O)O(alkO)_nSO_3$, in which R represents a linear or branched, aliphatic, saturated and/or unsaturated alkyl functional group having 6 to 22 C atoms, alk represents $CH_2CH_2$, $CHCH_3CH_2$, and/or $CH_2CHCH_3$, and n represents a number from 0.5 to 5;

monoglyceride sulfates and monoglyceride ether sulfates.

Preferred anionic surfactants are alkyl sulfates, alkyl ether sulfates, and ether carboxylic acids having 10 to 18 carbon atoms in the alkyl group and up to 12 glycol ether groups in the molecule.

Surface-active compounds that carry, in the molecule, at least one quaternary ammonium group and at least one carboxylate, sulfonate, or sulfate group are referred to as zwitterionic surfactants. Particularly suitable zwitterionic surfactants are the so-called betaines, such as the N-alkyl-N,N-dimethyl ammonium glycinates, e.g., cocoalkyldimethyl ammonium glycinate, N-acylaminopropyl-N,N-dimethyl ammonium glycinates, e.g., cocoacylaminopropyldimethyl ammonium glycinate, and 2-alkyl-3-carboxymethyl-3-hydroxyethylimidazolines having in each case 8 to 18 carbon atoms in the alkyl or acyl group, and cocoacylaminoethyl hydroxyethyl carboxymethyl glycinate. A preferred zwitterionic surfactant is the fatty acid amide derivative known under the INCI name, Cocamidopropyl Betaine.

Amphoteric surfactants are understood to be surface-active compounds which, in addition to a $C_8$-$C_{24}$ alkyl or acyl group, also contain at least one free amino group and at least one —COOH or —$SO_3H$ group in the molecule and are capable of forming inner salts. Examples of suitable amphoteric surfactants are N-alkylglycines, N-alkylpropionic acids, N-alkylaminobutyric acids, N-alkyliminodipropionic acids, N-hydroxyethyl-N-alkylamidopropyl glycines, N-alkyltaurines, N-alkylsarcosines, 2-alkylaminopropionic acids, and alkylamino acetic acids having in each case about 8 to 24 carbon atoms in the alkyl group. Particularly preferred amphoteric surfactants are N-cocoalkylaminopropionate, cocoacylaminoethylaminopropionate, and $C_{12}$-$C_{18}$ acyl sarcosine.

It has also proven to be advantageous if the coloring and lightening agents according to the invention contain further, non-ionogenic surface-active substances. Non-ionic surfactants contain, as a hydrophilic group, for example a polyol group, a polyalkylene glycol ether group, or a combination of polyol group and polyglycol ether group. Such compounds include, for example, addition products of 1 to 50 mol of ethylene oxide and/or 0 to 5 mol of propylene oxide to linear and branched fatty alcohols having 8 to 30 carbon atoms, such as for example lauryl, myristyl, cetyl, but also stearyl, isostearyl, and oleyl alcohol to fatty acids having 8 to 30 carbon atoms and to alkylphenols having 8 to 15 carbon atoms in the alkyl group, addition products end-capped with a methyl- or $C_2$-$C_6$ alkyl functional group of 1 to 50 mol ethylene oxide alkyl and/or 0 to 5 mol propylene oxide to linear and branched fatty alcohols with 8 to 30 carbon atoms, to fatty acids with 8 to 30 carbon atoms, and to alkylphenols with 8 to 15 carbon atoms in the alkyl group, such as those types available under the trade names, Dehydol® LS, Dehydol® LT (Cognis), polyglycerol esters and alkoxylated polyglycerol esters, such as for example poly(3)glycerol diisostearate (commercial product: Lameform® TGI (Henkel)) and poly(2)glycerol polyhydroxystearate (commercial product: Dehymuls® PGPH (Henkel)), polyol fatty acid esters, such as the commercial product, Hydagen® HSP (Cognis) or Sovermol-types (Cognis), more highly alkoxylated, preferably propoxylated, and in particular ethoxylated mono-, di-, and triglycerides, such as glycerol monolaurate+20 ethylene oxide and glycerol monostearate+20 ethylene oxide, amine oxides, hydroxy mixed ethers, sorbitan fatty acid esters and addition products of ethylene oxide to sorbitan fatty acid esters, such as polysorbates and sorbitol monolaurate+20 mol ethylene oxide (EO), sugar fatty acid esters and addition products of ethylene oxide to sugar fatty acid esters, addition products of ethylene oxide to fatty acid alkanolamides and fatty amines, fatty acid-N-alkyl glucamides, alkylphenols and alkylphenol alkoxylates having 6 to 21, and in particular 6 to 15, carbon atoms in the alkyl chain and 1 to 30 ethylene oxide and/or propylene oxide units. Preferred representatives of this class include nonylphenol+9 EO and octylphenol+8 EO;

alkyl polyglycosides corresponding to the general formula RO—$(Z)_x$, where R denotes an alkyl, Z denotes a sugar, and x denotes the number of sugar units. Alkyl polyglycosides usable according to the present invention may contain only one specific alkyl functional group R. However, these compounds are normally prepared from natural fats and oils or mineral oils. In this case, the alkyl functional groups R are present as mixtures corresponding to the starting compounds or to the particular work-up of these compounds.

Particularly suitable non-ionic surfactants are $C_8$-$C_{22}$ alkyl monoglycosides and alkyl oligoglycosides and their ethoxylated analogs. In particular, non-ethoxylated compounds have proven to be particularly suitable.

Particularly preferred are those alkyl polyglycosides of the formula RO—$(Z)_x$, where R substantially consists of $C_8$ and $C_{10}$ alkyl groups,
substantially consists of $C_{12}$ and $C_{14}$ alkyl groups,
substantially consists of $C_8$ to $C_{16}$ alkyl groups or
substantially consists of $C_{12}$ to $C_{16}$ alkyl groups or
substantially consists of $C_{16}$ to $C_{18}$ alkyl groups.

These compounds are characterized in that any mono- or oligosaccharides can be used as sugar building block Z. Usually, sugars with 5 or 6 carbon atoms as well as the corresponding oligosaccharides are used. Such sugars are, for example, glucose, fructose, galactose, arabinose, ribose, xylose, lyxose, allose, altrose, mannose, gulose, idose, talose, and sucrose. Preferred sugar building blocks are glucose, fructose, galactose, arabinose, and sucrose; glucose is particularly preferred.

The alkylpolyglycosides which can be used according to the invention contain on average 1.1 to 5 sugar units. Alkylpolyglycosides having x values of 1.1 to 2.0 are preferred. Very particular preference is given to alkylglycosides in which x is 1.1 to 1.8.

The alkoxylated homologs of said alkylpolyglycosides can also be used according to the invention. These homologs may contain on average up to 10 ethylene oxide and/or propylene oxide units per alkylglycoside unit.

Addition products of alkylene oxide to saturated linear fatty alcohols and fatty acids containing from 2 to 30 mol ethylene oxide per mol of fatty alcohol or acid have proved to be suitable as further preferred non-ionic surfactants. Preparations with excellent properties are likewise obtained if they contain fatty acid esters of ethoxylated glycerol as the non-ionic surfactants.

Particularly preferred non-ionogenic surface-active substances are, because of the simple processability, substances which are commercially available in pure form as solids or liquids. In this context, the definition for purity does not refer to chemically pure compounds. Rather—particularly if the products have a natural base—mixtures of different homologs can be used, e.g., with different alkyl chain lengths, as obtained in products based upon natural fats and oils. Mixtures of different degrees of alkoxylation are usually also present in alkoxylated products. In this context, the term, purity, refers instead to the fact that the selected substances are preferably to be free of solvents, controls, and other accompanying substances.

Products with a "normal" homolog distribution as well as those with a narrow homolog distribution may be used as surfactants which are addition products of ethylene and/or propylene oxide to fatty alcohols or derivatives of these addition products. "Normal" homolog distribution is to be understood in this case as mixtures of homologs which are obtained when reacting fatty alcohol and alkylene oxide using alkali metals, alkali metal hydroxides, or alkali metal alkoxides as catalysts. In contrast, a narrow homolog distribution is obtained when hydrotalcites, alkaline-earth metal salts of ether carboxylic acids, alkaline-earth metal oxides, hydroxides, or alkoxides, for example, are used as catalysts. The use of products with a narrow homolog distribution range may be preferred.

The anionic, non-ionic, zwitterionic, or amphoteric surfactants are used in amounts of 0.1 to 45 wt %, preferably 1 to 30 wt %, and very particularly preferably 1 to 15 wt %, relative to the total quantity of the ready-to-use agent.

Also preferred according to the invention are cationic surfactants of the quaternary ammonium compound, esterquat, and amidoamine type. Preferred quaternary ammonium compounds are ammonium halides, and in particular chlorides and bromides, such as alkyl trimethyl ammonium chlorides, dialkyl dimethyl ammonium chlorides, and trialkyl methyl ammonium chlorides, e.g., cetyl trimethyl ammonium chloride, stearyl trimethyl ammonium chloride, distearyl dimethyl ammonium chloride, lauryl dimethyl ammonium chloride, lauryl dimethyl benzyl ammonium chloride, and tricetyl methyl ammonium chloride, and the imidazolium compounds known under the INCI names, Quaternium-27 and Quaternium-83. The long alkyl chains of the aforementioned surfactants preferably have 10 to 18 carbon atoms. The quaternized protein hydrolysates represent other cationic surfactants that can be used according to the invention.

The alkylamidoamines are usually prepared by amidation of natural or synthetic fatty acids and fatty acid fractions with dialkylaminoamines and are characterized by their good biodegradability alongside a good conditioning effect. One compound from this substance group which is particularly suitable according to the invention is the stearamidopropyl dimethylamine available commercially under the name, Tegoamid® S 18.

Also highly biodegradable are quaternary ester compounds—so-called "esterquats." Esterquats are known substances that contain both at least one ester function and at least one quaternary ammonium group as structural element. Preferred esterquats are quaternized ester salts of fatty acids with triethanolamine, quaternized ester salts of fatty acids with diethanolalkylamines and quaternized ester salts of fatty acids with 1,2-dihydroxypropyldialkylamines. Such products are sold, for example, under the trademarks, Stepantex®, Dehyquart®, and Armocare®. The products, Armocare® VGH-70, an N,N-bis(2-palmitoyloxyethyl)dimethyl ammonium chloride, and Dehyquart® F-75, Dehyquart® C-4046, Dehyquart® L80, and Dehyquart® AU-35, are examples of such esterquats.

The cationic surfactants are contained in the agents used according to the invention preferably in amounts of 0.05 to 10 wt %, relative to the total agent. Quantities of 0.1 to 5 wt % are particularly preferred.

In one preferred embodiment, preference may be given to non-ionic, zwitterionic, and/or amphoteric surfactants and mixtures thereof.

In a further preferred embodiment, the effect of the active ingredient according to the invention can be enhanced by emulsifiers. Such emulsifiers are for example, addition products of 4 to 30 mol of ethylene oxide and/or 0 to 5 mol of propylene oxide to linear fatty alcohols having 8 to 22 C atoms, to fatty acids having 12 to 22 C atoms, and to alkylphenols having 8 to 15 C atoms in the alkyl group, $C_{12}$-$C_{22}$ fatty acid monoesters and diesters of addition products of 1 to 30 mol of ethylene oxide to polyols having 3 to 6 carbon atoms, and in particular to glycerol, ethylene oxide and polyglycerol addition products to methyl glucoside fatty acid esters, fatty acid alkanolamides, and fatty acid glucamides, $C_8$-$C_{22}$ alkyl mono- and oligoglycosides and the ethoxylated analogs thereof, wherein preference is given to degrees of oligomerization of 1.1 to 5, and in particular 1.2 to 2.0, and glucose as the sugar component, mixtures of alkyl (oligo) glucosides and fatty alcohols—for example, the commercially available product, Montanov® 68, addition products of 5 to 60 mol ethylene oxide to castor oil and hydrogenated castor oil, partial esters of polyols having 3 to 6 carbon atoms with saturated fatty acids having 8 to 22 carbon atoms, sterols, wherein sterols are understood to mean a group of steroids which carry a hydroxyl group on carbon atom 3 of the steroid backbone and are isolated both from animal tissue (zoosterols) and plant fats (phytosterols). Examples of zoosterols include cholesterol and lanosterol. Examples of suitable phytosterols include ergosterol, stigmasterol, and sitosterol. There are also sterols that are isolated from fungi and yeasts (so-called mycosterols).

phospholipids, and especially glucose phospholipids, which are obtained for example as lecithins or phosphatidylcholines from, for example, egg yolk or plant seeds (for example, soybeans), fatty acid esters of sugars and sugar alcohols, such as sorbitol, polyglycerols and polyglycerol derivatives, such as for example polyglycerol poly-12-hydroxystearate (commercial product: Dehymuls® PGPH), linear and branched fatty acids having 8 to 30 carbon atoms, and the Na, K, ammonium, Ca, Mg, and Zn salts thereof.

The agents according to the invention contain the emulsifiers preferably in amounts of 0.1 to 25 wt %, and in particular 0.5 to 15 wt %, relative to the total quantity of the ready-to-use agent.

According to the invention, particular preference may be given to non-ionogenic emulsifiers and surfactants having an HLB value of 10-15. Among these emulsifier types, very particular preference may be given to those emulsifiers which contain no ethylene oxide and/or propylene oxide in the molecule.

Further work has shown that the oxidative formation of intense colorations from the components (a) and (b) functions in particular in the cosmetic carrier formulations which do not have an excessively high fat component content. A strong color effect was then observed in particular if, relative to the total weight of the agent, the total amount of fat components contained in the agent was below 25 wt %, preferably below 20 wt %, further preferably below 15 wt %, and very particularly preferably below 13 wt %.

In a further preferred embodiment, an agent according to the invention is characterized in that, relative to the total weight of the agent, the total amount of fat components contained In the agent is below 25 wt %, preferably below 20 wt %, further preferably below 15 wt %, and very particularly preferably below 13 wt %.

Fat components in the sense of the invention are understood to be organic compounds with a solubility in water of less than 1 wt %, and preferably less than 0.1 wt %, at room temperature (22° C.) and atmospheric pressure (760 mmHg).

Only uncharged (i.e., non-ionic) compounds explicitly fall under the definition of fat components. Fat components have at least one saturated or unsaturated alkyl group having at least 8 C atoms. The molecular weight of the fat component is at most 5,000 g/mol, preferably at most 2,500 g/mol, and particularly preferably at most 1,000 g/mol. The fat components are either polyoxyalkylated or polyglycerylated compounds.

In this context, fat components are understood to be components from the group of $C_{12}$-$C_{30}$ fatty alcohols, $C_{12}$-$C_{30}$ fatty acid triglycerides, and/or hydrocarbons. In the sense of the present invention, only non-ionic substances are explicitly considered fat components. Charged compounds, such as fatty acids and salts thereof, are not understood to be fat components.

$C_{12}$-$C_{30}$ fatty alcohols can be saturated, mono- or polyunsaturated, linear or branched fatty alcohols having 12 to 30 C atoms.

Examples of preferred linear saturated $C_{12}$-$C_{30}$ fatty alcohols are dodecan-1-ol (dodecyl alcohol, lauryl alcohol), tetradecan-1-ol (tetradecyl alcohol, myristyl alcohol), hexadecan-1-ol (hexadecyl alcohol, cetyl alcohol, palmityl alcohol), octadecan-1-ol (octadecyl alcohol, stearyl alcohol), arachyl alcohol (eicosan-1-ol), heneicosyl alcohol (heneicosan-1-ol), and/or behenyl alcohol (docosan-1-ol).

Linear unsaturated fatty alcohols are, for example, (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linolenoyl alcohol), gadoleyl alcohol ((9Z)-eicos-9-en-1-ol), arachidone alcohol ((5Z,8Z,11Z,14Z)-eicosa-5,8,11,14-tetraen-1-ol), erucyl alcohol ((13Z)-docos-13-en-1-ol), and/or brassidyl alcohol ((13E)-docosen-1-ol).

By a $C_{12}$-$C_{30}$ fatty acid triglyceride, in the context of the present invention, are understood the triesters of trivalent alcohol glycerol with three equivalents of fatty acid. Both structurally similar and different fatty acids may be involved in the ester formation within a triglyceride molecule.

According to the invention, fatty acids are to be understood as saturated or unsaturated, unbranched or branched, unsubstituted or substituted $C_{12}$-$C_{30}$ carboxylic acids. Unsaturated fatty acids may be mono-unsaturated or polyunsaturated. With an unsaturated fatty acid, the C—C double bond(s) thereof may have the cis or trans configuration.

By way of example, esters originating from glycerol having a fatty acid can be named as fatty acid triglycerides, wherein the fatty acid is selected from the group consisting of dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z,12Z)-octadeca-9,12-dienoic acid], linolenic acid [(9Z,12Z,15Z)-octadeca-9,12,15-trienoic acid], eleostearic acid [(9Z,11E,13E)-octadeca-9,11,3-trienoic acid], arachidonic acid [(5Z,8Z,11Z,14Z)-eicosa-5,8,11,14-tetraenoic acid], and/or nervonic acid [(15Z)-tetracos-15-enoic acid].

The fatty acid triglycerides may also be of natural origin. The fatty acid triglycerides or mixtures thereof, e.g., corresponding natural fatty acid triglycerides, occurring in soybean oil, groundnut oil, olive oil, sunflower oil, macadamia nut oil, moringa oil, apricot kernel oil, marula oil, and/or optionally hydrogenated castor oil.

Hydrocarbons are compounds having 8 to 80 C atoms composed exclusively of carbon and hydrogen atoms. Especially preferred in this context are aliphatic hydrocarbons, such as mineral oils, liquid paraffin oils (e.g., paraffinum liquidum or paraffinum perliquidum), isoparaffin oils, semi-solid paraffin oils, paraffin waxes, solid paraffin (paraffinum solidum), Vaseline, and polydecene.

In this respect, liquid paraffin oils (paraffinum liquidum and paraffinum perliquidum) have proven to be particularly suitable. The hydrocarbon is very particularly preferably paraffinum liquidum, also referred to as white oil. Paraffinum liquidum is a mixture of purified, saturated, aliphatic hydrocarbons, consisting mainly of hydrocarbon chains having a C-chain distribution of 25 to 35 C atoms.

Furthermore, it has proved advantageous if the according to the invention contain at least one stabilizer or complexer. Conventional complexing agents and stabilizers that are preferred in the context of the present invention are, for example, polyoxycarboxylic acids, polyamines, ethylene diamine tetraacetic acid (EDTA), N-hydroxyethyl ethylene diamine triacetic acid, diethylene triamine pentaacetic acid (DTPA), ethylene diamine disuccinic acid (EDDS), hydroxyethyliminodiacetic acid, nitridodiacetic acid-3-propionic acid, isoserindiacetic acid, N,N-di-(2-hydroxyethyl) glycine, N-(1,2-dicarboxy-2-hydroxyethyl)glycine, N-(1,2-dicarboxy-2-hydroxyethyl) aspartic acid or nitrilotriacetic acid (NTA), ethylene diamine diglutaric acid (EDGA), 2-hydroxypropylene diamine disuccinic acid (HPDS), glycinamide-N,N'-disuccinic acid (GADS), ethylene diamine-N—N'-diglutaric acid (EDDG), 2-hydroxypropylene diamine-N—N'-disuccinic acid (HPDDS), diaminoalkyldi-(sulfosuccinic acid) (DDS), ethylene dicysteic acid (EDC), ethylene diamine-N—N'-bis-(ortho-hydroxyphenyl)acetic acid (EDDHA), N-2-hydroxyethylamine-N,N-diacetic acid, glyceryliminodiacetic acid, iminodiacetic acid-N-2-hydroxypropyl sulfonic acid, aspartic acid-N-carboxymethyl-N-2,5-hydroxypropyl-3-sulfonic acid, β-alanine-N,N'-diacetic acid, aspartic acid-N,N'-diacetic acid, aspartic acid-N-monoacetic acid, dipicolinic acid, and salts and/or derivatives thereof, geminal diphosphonic acids such as 1-hydroxyethane-1,1-diphosphonic acid (HEDP), the higher homologs thereof with up to 8 carbon atoms, and also derivatives thereof containing hydroxy or amino groups and 1-aminoethane-1,1-diphosphonic acid, the higher homologs thereof with up to 8 carbon atoms, and also derivatives containing hydroxy or amino groups, aminophosphonic acids such as ethylene diamine tetra(methylene phosphonic acid) (EDTMP), diethylene triamine penta(methylene phosphonic acid) (DTPMP) and higher homologs thereof, or nitrilotris(methylene phosphonic acid), phosphonopolycarboxylic acids such as 2-phosphonobutane-1,2,4-tricarboxylic acid, cyclodextrins, and alkali stannates (sodium stannate), alkalipyrophosphates (tetrasodiumpyrophosphate, disodiumpyrophosphate), alkaliphosphates (sodium phosphate), and phosphoric acid and salts thereof.

In the alkali pH values required according to the invention of the treatment solutions, these complexers are present at least partially as anions. It does not matter whether they are introduced in the form of acids or in the form of salts. If used as salts, preference is given to alkali, ammonium, or alkylammonium salts, and in particular sodium salts.

Complexers preferred according to the invention are nitrogen-containing polycarboxylic acids, and in particular EDTA, and phosphonates, and preferably hydroxyalkane or aminoalkane phosphonates and in particular 1-hydroxyethane-1,1-diphosphonate (HEDP) or the di- or tetra sodium salt thereof, and/or ethylene diamine tetramethylene phosphonate (EDTMP) or the hexasodium salt thereof, and/or diethylene triamine pentamethylene phosphonate (DTPMP) or the hepta- or octasodium salt thereof.

The dyes according to the invention can preferably contain further auxiliary substances and additives. For instance, it has proven to be preferred according to the invention if the agents contain at least one thickener. There are no basic restrictions with regard to these thickeners. Both organic and purely inorganic thickeners may be used.

According to a first preferred embodiment, the thickening agent is an anionic, synthetic polymer. Preferred anionic groups are the carboxylate group and the sulfonate group.

Examples of anionic monomers of which the polymeric anionic thickener may consist are acrylic acid, methacrylic acid, crotonic acid, itaconic acid, maleic anhydride, and 2-acrylamido-2-methylpropanesulfonic acid. Here, the acidic groups may be present wholly or partly as sodium-, potassium-, ammonium-, mono- or triethanol ammonium salt. Preferred monomers are maleic acid anhydride, and in particular, 2-acrylamido-2-methylpropane sulfonic acid and acrylic acid.

Preferred anionic homopolymers are uncrosslinked and crosslinked polyacrylic acids. Here, allyl ethers of pentaerythritol, sucrose, and propylene may be preferred crosslinking agents. Such compounds are commercially available, for example, under the trade name, Carbopol®. Also preferred is the homopolymer of 2-acrylamido-2-methyl propane sulfonic acid, which is commercially available, for example, under the name, Rheothik® 11-80.

Within this first embodiment, it may further be preferred to use copolymers of at least one anionic monomer and at least one non-ionic monomer. With regard to the anionic monomers, reference is made to the substances listed above. Preferred non-ionic monomers are acrylamide, methacrylamide, acrylic acid esters, methacrylic acid esters, itaconic acid monoesters and diesters, vinyl pyrrolidinone, vinyl ethers, and vinyl esters.

The anionic acrylic acid and/or methacrylic acid polymers or copolymers are contained in the agents according to the invention preferably in an amount of 0.1 to 10 wt %, and particularly preferably 1 to 5 wt %, in each case relative to the weight of the agent.

Preferred anionic copolymers are, for example, copolymers of acrylic acid, methacrylic acid, or their $C_1$-$C_6$ alkyl esters, such as are marketed under the INCI name, acrylate copolymers. One preferred commercial product is Aculyn® 33 from Rohm & Haas, for example. However, copolymers of acrylic acid, methacrylic acid or their $C_1$-$C_6$ alkyl esters and the esters of an ethylenically unsaturated acid and an alkoxylated fatty alcohol are further preferred. Suitable ethylenically unsaturated acids are in particular acrylic acid, methacrylic acid, and itaconic acid, and suitable alkoxylated fatty alcohols are in particular Steareth-20 or Ceteth-20. Such copolymers are marketed by Rohm & Haas under the trade name, Aculyn® 22, and by National Starch under the trade names, Structure® 2001 and Structure® 3001.

Preferred anionic copolymers are, furthermore, acrylic acid-acrylamide copolymers as well as in particular polyacrylamide copolymers with monomers containing a sulfonic acid group. A particularly preferred anionic copolymer consists of 70 to 55 mol % acrylamide and 30 to 45 mol % 2-acrylamido-2-methylpropane sulfonic acid, wherein the sulfonic acid group is wholly or partially present as a sodium, potassium, ammonium, mono- or triethanol ammonium salt. This copolymer can also be crosslinked, wherein preferably polyolefinically unsaturated compounds such as tetraallyloxythane, allylsucrose, allylpentaerythritol, and methylene-bisacrylamide are used as crosslinking agents. Such a polymer is contained in the commercial products, Sepigel® 305 and Simulgel® 600, from the company SEPPIC. The use of these compounds, which contain a hydrocarbon mixture ($C_{13}$-$C_{14}$ isoparaffin or isohexadecane) and a non-ionic emulsifier (laureth-7 or polysorbate-80) in addition to the polymer components, has proved to be particularly advantageous in the context of the teaching of the invention.

Also, polymers of maleic acid anhydride and methyl vinyl ether, and in particular those with crosslinks, are preferred thickeners. The maleic acid methyl vinyl ether copolymer crosslinked with 1,9-decadiene is available under the name, Stabileze® QM.

According to another embodiment, the thickener is a cationic synthetic polymer. Preferred cationic groups are quaternary ammonium groups. In particular, those polymers in which the quaternary ammonium group is bonded to a polymer backbone built-up of acrylic acid, methacrylic acid, or derivatives thereof via a $C_1$-$C_4$ hydrocarbon group have been found to be particularly suitable.

Homopolymers of general formula (HP-1), (HP-1)

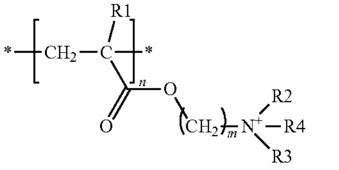

in which R1=—H or —$CH_3$, R2, R3, and R4 independently of one another are selected from $C_1$-$C_4$ alkyl, alkenyl, or hydroxyalkyl groups, m=1, 2, 3, or 4, n is a natural number, and $X^-$ is a physiologically tolerated organic or inorganic anion, as well as copolymers consisting substantially of the monomer units shown in formula (HP-1) and non-ionogenic monomer units, are particularly preferred cationic polymeric gel formers. In the context of these polymers, those are preferred according to the invention for which at least one of the following conditions applies:

R1 represents a methyl group,

R2, R3, and R4 are methyl groups, m has the value 2.

Halide ions, sulfate ions, phosphate ions, methosulfate ions, as well as organic ions, such as lactate, citrate, tartrate, and acetate ions, are considered for example, physiologically tolerated counter ions $X^-$. Halide ions are preferred, and particularly chloride.

A particularly suitable homopolymer is the poly(methacryloxyethyltrimethyl ammonium) chloride (crosslinked, if desired) having the INCI name, Polyquaternium-37. The crosslinking can be carried out, if desired, with the help of olefinically polyunsaturated compounds, e.g., divinyl benzene, tetraallyloxyethane, methylene bisacrylamide, diallyl ether, polyallyl polyglyceryl ether, or allyl ethers of sugars or sugar derivatives, such as erythritol, pentaerythritol, arabitol, mannitol, sorbitol, sucrose, or glucose. Methylene bisacrylamide is a preferred crosslinking agent.

The homopolymer is preferably used in the form of a non-aqueous polymer dispersion, which should not have a polymer content of less than 30 wt %. Such polymer dispersions are commercially available under the names, Salcare® SC 95 (approx. 50% polymer content, further component: mineral oil (INCI name: mineral oil) and tridecyl-polyoxypropylene polyoxyethylene ether (INCI name: PPG-1-trideceth-6)) and Salcare® SC 96 (approx. 50% polymer content, further components: mixture of diesters of propylene glycol with a mixture of caprylic and capric acid (INCI name: propylene glycol dicaprylate/dicaprate) and tridecyl-polyoxypropylene polyoxyethylene ether (INCI name: PPG-1-trideceth-6)).

Copolymers having monomer units according to formula (HP-1) contain as non-ionogenic monomer units preferably acrylamide, methacrylamide, acrylic acid $C_1$-$C_4$ alkyl ester, and methacrylic acid $C_1$-$C_4$ alkyl ester. Among these non-ionic monomers, acrylamide is particularly preferred. These copolymers can also be crosslinked like the homopolymers described above. A preferred copolymer according to the invention is a crosslinked acrylamide methacryl oxyethyl trimethyl ammonium chloride copolymer. Such copolymers, in which the monomers are present in a weight ratio of about 20:80, are commercially available as approx. 50% non-aqueous polymer dispersion under the name, Salcare® SC 92.

In another preferred embodiment, naturally occurring thickeners are used. Preferred thickeners of this embodiment are, for example, non-ionic guar gums. According to the invention, both modified and unmodified guar gums can be used. Unmodified guar gums are marketed, for example, under the trade name, Jaguar® C from Rhone Poulenc. Modified guar gums which are preferred according to the invention contain $C_1$-$C_6$ hydroxyalkyl groups. The groups are preferably hydroxymethyl, hydroxyethyl, hydroxypropyl, and hydroxybutyl. Such modified guar gums are well known in the art and can be prepared, for example, by reacting the guar gums with alkylene oxides. The degree of hydroxyalkylation, which corresponds to the number of used alkylene oxide molecules in proportion to the number of the free hydroxyl groups of guar gum, is preferably between 0.4 to 1.2. Such modified guar gums are commercially available under the trade names, Jaguar® HP8, Jaguar® HP60, Jaguar® HP120, Jaguar® DC 293, and Jaguar® HP105, from Rhone Poulenc.

Further suitable natural thickening agents are also already known from the prior art.

According to this embodiment, biosaccharide gums of microbial origin, such as scleroglucan gums or xanthan gums, gums from plant exudates, such as gum arabic, ghatti gum, karaya gum, tragacanth gum, carrageenan gum, agar-agar, locust bean gum, pectins, alginates, starch fractions and derivatives, such as amylose, amylopectin and dextrins, cellulose derivatives such as methyl cellulose, carboxyalkyl celluloses, and hydroxyalkyl celluloses, are preferred.

Preferred hydroxyalkyl celluloses are, in particular, the hydroxyethyl celluloses, which are marketed under the names, Cellosize® from Amerchol and Natrosol® from Hercules. Suitable carboxyalkyl celluloses are in particular the carboxymethyl celluloses as marketed under the names, Blanose® from Aqualon, Aquasorb® and Ambergum® from Hercules, and Cellgon® from Montello.

Preference is also given to starch and derivatives thereof. Starch is a storage material of plants, which occurs mainly in tubers and roots, in grain seeds, and in fruits, and can be obtained from a variety of plants in high yield. The polysaccharide, which is insoluble in cold water and forms a colloidal solution in boiling water, for example, can be obtained from potatoes, manioc, sweet potatoes, maranta, corn, grains, rice, legumes such as peas and beans, bananas, or the marrow of certain types of palm (for example, the sago palm). According to the invention, natural, plant-derived starches and/or chemically or physically modified starches can be used. Modification can be achieved, for example, by introducing different functional groups on one or more of the hydroxyl groups of the starch. These are usually esters, ethers, or amides of starch having optionally substituted $C_1$-$C_{40}$ functional groups. Particularly advantageous is an etherified corn starch with 2-hydroxypropyl group, as marketed, for example, by National Starch under the trade name, Amaze®.

However, non-ionic, fully-synthetic polymers, such as for example polyvinyl alcohol or polyvinyl pyrrolidone, can also be used as thickening agents according to the invention.

Preferred non-ionic, fully-synthetic polymers are marketed for example by BASF under the trade name, Luviskol®. Such non-ionic polymers also allow, in addition to their excellent thickening properties, a significant improvement in the sensory feeling of the resulting preparations.

As inorganic thickeners, phyllosilicates (polymeric, crystalline sodium disilicates) have proven to be particularly suitable in the context of the present invention. In particular, clays, and in particular, magnesium aluminum silicates, such as bentonite, particularly smectites, such as montmorillonite or hectorite, which may also be optionally suitably modified, and synthetic phyllosilicates, such as the magnesium phyllosilicates marketed by the company Süd Chemie under the trade name, Optigel®, are preferred.

To further increase the performance of the oxidative dyes, at least one optionally hydrated $SiO_2$ compound is additionally preferably added. It may be preferred according to the invention to use the optionally hydrated $SiO_2$ compounds in amounts of 0.05 wt % to 15 wt %, particularly preferably in amounts of 0.15 wt % to 10 wt %, and very particularly preferably in amounts of 0.2 wt % to 5 wt %, in each case relative to the agent according to the invention. The specified amounts in each case reflect here the content of the $SiO_2$ compounds (without the water content thereof) in the agents.

With regard to the optionally hydrated $SiO_2$ compounds, the present invention is in principle subject to no limitations. Preference is given to silicic acids, oligomers thereof and polymers thereof, and also salts thereof. Preferred salts are the alkali metal salts, and in particular the potassium and sodium salts. The sodium salts are very particularly preferred.

The optionally hydrated $SiO_2$ compounds may be present in different forms. According to the invention, preference is given to using the $SiO_2$ compounds in the form of silica gels, or particularly preferably as water glass. These $SiO_2$ compounds may sometimes be present in aqueous solution.

Very particularly preferred according to the invention are water glasses, which are formed from a silicate of formula $(SiO_2)_n(Na_2O)_m(K_2O)_p$, where n represents a positive rational number, and m and p, independently of one another, represent a positive rational number or 0, with the proviso that at least one of the parameters m or p be different from 0, and the ratio between n and the sum of m and p be between 1:4 and 4:1. Preference is given to metasilicates in which the ratio between n and the sum of m and p is 1.2 or below.

Besides the components described by the empirical formula, the water glasses may also contain further additives in small amounts, such as for example phosphates or magnesium salts.

Water glasses which are particularly preferred according to the invention are marketed, inter alia, by Henkel under the names, Ferrosil® 119, Natronwasserglas 40/42, Portil® A, Portil® AW, and Portil® W, and by Akzo under the name, Britesil® C20.

The oxidative dyeing agents are preferably packaged as flowable preparations.

The agents according to the invention may also contain further active substances, auxiliaries, and additives, such as for example,

- non-ionic polymers, such as for example vinyl pyrrolidinone/vinyl acrylate copolymers, polyvinyl pyrrolidinone, vinyl pyrrolidinone/vinyl acetate copolymers, polyethylene glycols, and polysiloxanes;
- silicones, such as volatile or non-volatile, straight-chain, branched or cyclic, crosslinked or non-crosslinked polyalkylsiloxanes (such as dimethicones or cyclomethicones), polyarylsiloxanes and/or polyalkylarylsiloxanes, and in particular polysiloxanes having organofunctional groups, such as substituted or unsubstituted amines (amodimethicones), carboxyl, alkoxy, and/or hydroxyl groups (dimethicone copolyols), linear polysiloxane (A)-polyoxyalkylene (B) block copolymers, grafted silicone polymers having a non-silicone-containing organic backbone or having a polysiloxane backbone, such as for example the commercial product, Abil B 8832, from the company Degussa, which is marketed under the INCI name, Bis-PEG/PPG-20/20 Dimethicone, or mixtures thereof;
- cationic polymers, such as quaternized cellulose ethers, polysiloxanes with quaternary groups, dimethyldiallyl ammonium chloride polymers, acrylamide-dimethyldiallyl ammonium chloride copolymers, dimethylaminoethyl methacrylate vinyl pyrrolidinone copolymers quaternized with diethyl sulfate, vinyl pyrrolidinone-imidazolinium-methochloride copolymers, and quaternized polyvinyl alcohol;
- zwitterionic and amphoteric polymers, such as for example acrylamidopropyl trimethyl ammonium chloride/acrylate copolymers and octylacrylamide/methyl methacrylate/tert-butylaminoethyl methacrylate/2-hydroxypropyl methacrylate copolymers, diallyldimethyl ammonium chloride/acrylate copolymers, t-butylaminoethyl methacrylate/N-(1,1,3,3-tetramethylbutyl) acrylamide/acrylate(/methacrylate) copolymers;
- anionic polymers, such as for example polyacrylic acids, crosslinked polyacrylic acids, vinyl acetate/crotonic acid copolymers, vinyl pyrrolidinone/vinyl acrylate copolymers, vinyl acetate/butyl maleate/isobornyl acrylate copolymers, methyl vinyl ether/maleic anhydride copolymers, and acrylic acid/ethyl acrylate/N-t-butylacrylamide terpolymers,
- further thickeners, such as agar-agar, guar gum, alginates, xanthan gum, gum arabic, karaya gum, locust bean flour, linseed gum, dextrans, cellulose derivatives, e.g., methyl cellulose, hydroxyalkyl cellulose, and carboxymethyl cellulose, starch fractions and derivatives, such as amylose, amylopectin, and dextrins, clays, such as for example bentonite or fully-synthetic hydrocolloids, such as for example polyvinyl alcohol,
- structurants, such as glucose, maleic acid, and lactic acid,
- hair-conditioning compounds, such as phospholipids, for example soya lecithin, egg lecithin, and cephalins, as well as silicone oils,
- perfume oils, dimethyl isosorbide, and cyclodextrins,
- solvents and solubilizers, such as ethanol, isopropanol, ethylene glycol, propylene glycol, glycerol, and diethylene glycol,
- fiber-structure-improving active ingredients, and in particular mono-, di-, and oligosaccharides, such as, for example, glucose, galactose, fructose, fruit sugar, and lactose,
- quaternized amines, such as methyl-1-alkylamidoethyl-2-alkylimidazolinium methosulfate,
- defoaming agents, such as silicones,
- dyes for coloring the agent,
- anti-dandruff active substances such as piroctone olamine, zinc omadine, and climbazole,
- amino acids and oligopeptides, and in particular arginine and/or serine,
- protein hydrolysates of animal and/or plant origin, such as for example elastin, collagen, keratin, silk, and lactoprotein protein hydrolysates, or almond, rice, pea, potato, and wheat protein hydrolysates, as well as those in the form of their fatty acid condensation products or optionally anionically- or cationically-modified derivatives thereof, vegetable oils, for example macadamia nut oil, kukui nut oil, palm oil, amaranth seed oil, peach kernel oil, avocado oil, olive oil, coconut oil, rapeseed oil, sesame oil, jojoba oil, soybean oil, peanut oil, evening primrose oil, and tea tree oil, light stabilizers, and in particular derivatized benzophenones, cinnamic acid derivatives, and triazines, substances for adjusting the pH, such as for example conventional acids—in particular, edible acids and bases, active substances such as panthenol, pantothenic acid, pantolactone, allantoin, pyrrolidone carboxylic acids and salts thereof, and bisabololl, polyphenols, and in particular hydroxycinnamic acids, 6,7-dihydroxycoumarin, hydroxybenzoic acids, catechins, tannins, leucoanthocyanidins, anthocyanidins, flavanones, flavones, and flavonols, ceramides, and preferably the sphingolipids such as ceramide I, ceramide II, ceramide 1, ceramide 2, ceramide 3, ceramide 5, and ceramide 6, or pseudoceramides, such as in particular N—($C_8$-$C_{22}$-acyl)-($C_8$-$C_{22}$-acyl)-hydroxyproline, vitamins, provitamins, and vitamin precursors, and in particular those of groups A, $B_3$, $B_5$, $B_6$, C, E, F, and H, plant extracts, such as for example the extracts of aloe vera, angelica, anise, apricot, benzoin, bergamot, birch, nettle, calamus, blackcurrant, costus, hibiscus, oak bark, elemi, tarragon, pine needles, galbanum, geranium, ginseng, grapefruit, guaiac wood, green tea, hamamelis, restharrow, hops, coltsfoot, ginger root, iris, jasmine, chamomile, cardamom, clover, burdock root, pine, kiwi fruit, coconut, coriander, caraway, mountain pine, lavender, lemon grass, lily, lime, linden blossom, lychee, mace, malva, almond, mango, lemon balm, melon, meristem, myrrh, neroli, olibanum, opoponax, orange, patchouli, petitgrain, stone pine, wild thyme, rooibos, rose, rosemary, horse chestnut, sandalwood, sage, horsetail, yarrow, celery, spruce, thyme, juniper, vine leaves, hawthorn, wheat, lady's-smock, ylang-ylang, cedar, and lemon, cholesterol, consistency regulators, such as sugar esters, polyol esters, or polyol alkyl ethers, fats and waxes, such as spermaceti, beeswax, montan wax and paraffins, fatty acid alkanolamides, swelling and penetration agents, such as glycerol, propylene glycol monoethyl ether, carbonates, hydrogen carbonates, guanidines, ureas, and primary, secondary, and tertiary phosphates, turbidity agents, such as latex, styrene/PVP, and styrene/acrylamide copolymers, pearlescent agents, such as ethylene glycol mono- and distearate and PEG-3 distearate, pigments, stabilizing agent for hydrogen peroxide and other oxidizing agents, propellants such as propane-butane mixtures, $N_2O$, dimethyl ether, $CO_2$, and air, antioxidants.

The selection of these additional substances is made by the person skilled in the art according to the desired properties of the agents.

With respect to other optional components and the employed amounts of said components, reference is made expressly to relevant manuals known to the person skilled in the art, e.g., Kh. Schrader, Grundlagen and Rezepturen der Kosmetika, 2nd edition, Hüthig Buch Verlag, Heidelberg, 1989.

The additional active ingredients and auxiliaries are used in the agents according to the invention preferably in quantities of, in each case, 0.0001 to 10 wt %, and in particular of 0.0005 to 5 wt %, relative to the total weight of the application mixture.

Multi-Component Packaging Unit (Kit-Of-Parts)

The agents according to the invention are agents for oxidatively dyeing or dyeing and lightening hair. In the ready-to-use agent, the oxidation dye precursors react with the oxidizing agent to form the actual dyes. The agents according to the invention are therefore usually packaged as multi-component agents, and usually as two-component agents. The first component here contains the oxidation dye precursors (a) and isatin (b), as well as the alkalizing agent (c), which is mixed shortly before application with a second component containing the oxidizing agent (e). Usually, both components are mixed with one another in the range of 1:3 to 3:1, and preferably 1:2 to 2:1. This mixture of the component containing color cream and optionally alkalizing agent (preparation A) and the component containing oxidizing agent (preparation B) is referred to as the application mixture or the ready-to-use agent.

A second subject matter of the present invention is a multi-component packaging unit (kit-of-parts) for oxidatively coloring keratin fibers, and in particular human hair, comprising, packaged separately from one another, a first container having a dyeing agent (F), which contains
(a) at least one developer-type oxidation dye precursor, and
(b) isatin, and
(c) at least one alkalizing agent from the group consisting of ammonia, monoethanolamine, 2-amino-2-methylpropanol, arginine, lysine, ornithine, and histidine, and a second container having an oxidizing agent composition (Ox), which contains
(e) at least one oxidizing agent from the group consisting of hydrogen peroxide and its addition products to organic or inorganic compounds, wherein the components (a), (b), (c), and (e) having already been disclosed in detail in the description of the first subject matter of the invention.

Alternatively, the dyeing agent can also be referred to as color cream.

Method for Oxidatively Dyeing Keratin Fibers

The oxidative dyeing agent according to the invention of the first subject matter of the invention or the multicomponent packaging unit, the separately packaged components of which are used for producing this ready-to-use dyeing agent, are outstandingly suitable for use in corresponding dyeing methods.

A further subject matter of the present invention is therefore a method for oxidatively dyeing keratinous fibers, and in particular human hair, in which an agent, as disclosed in detail in the description of the first subject matter of the invention, is applied to the keratinous fibers and rinsed out again after an exposure time.

While the fibers are being exposed to the agent, it can be advantageous to support the dyeing process by applying heat. Heat can be applied by an external heat source, such as hot air from a hot-air blower, and also—particularly in the case of dyeing the hair of a living subject—by the body temperature of the subject. In the latter possibility, conventionally the part to be dyed is covered with a cap. In particular, the temperature during the exposure time is between 10° C. and 45° C., and in particular between 20° C. and 40° C. The dyes according to the invention already give intense colorations at physiologically tolerated temperatures of less than 45° C. Therefore, they are suitable particularly for coloring human hair.

What has been stated regarding the agent according to the invention applies, mutatis mutandis, to additional preferred embodiments of the multicomponent packaging unit and method according to the invention.

EXAMPLES

1. Production of the Formulations

The following recipes were produced. Unless otherwise noted, the quantitative data are given in weight percent in each case.

TABLE 1

| Color cream basic recipe | F (wt %) |
|---|---|
| Sodium cetearyl sulfate | 1.3 |
| 2-Octyldodecanol | 2.0 |
| Cetearyl alcohol | 14.9 |
| Glyceryl stearate | 5.4 |
| Glycerol | 2.0 |
| Cocoamidopropyl betaine (40% aqueous solution) | 1.8 |
| Mixture of oxidation dye precursors (mixture OFV) | according to Tables 3 and 4 |
| Ammonia (25% aqueous solution) | 6.0 |
| Sodium sulfite | 0.2 |
| Water (distilled) | up to 100 |

TABLE 2

| Oxidizing agent preparation | OX (wt %) |
|---|---|
| 1,2-propanediol | 0.5 |
| Paraffinum liquidum | 0.5 |
| Cetearyl alcohol | 4.0 |
| Ceteareth-20 | 1.2 |
| Hydrogen peroxide (50% aqueous solution) | 12.00 |
| Water (distilled) | up to 100 |

2. Application and Colorimetric Results

The base formulation for the color cream described in Table 1 was prepared. The mixtures of oxidation dye precursors described in Tables 3 and 4 were each incorporated into the color cream. Each of the color creams produced in this way was mixed in a quantitative ratio of 1:1 with the oxidizing agent preparation OX. The pH of the ready-to-use coloring agent thus produced was about 9.5. Subsequently, each of the ready-to-use dyeing agents was applied to a hair strand (Kerling, natural white) and left there for a period of 30 minutes. The application mixture was then rinsed out with a shampoo and dried. The hair strands were then measured colorimetrically (measurement of the lab values).

TABLE 3

(all figures in wt %, relative to the total weight of the color cream)

| Mixture OFV | F1 | F2 without RES | F3 | F4 without RES | F5 | F6 without RES |
|---|---|---|---|---|---|---|
| p-toluylene diamine (sulfate) | 0.85 | 0.55 | 0.41 | 1.16 | 1.86 | 4.66 |
| Resorcinol | 0.23 | — | 0.10 | — | 0.65 | — |
| 4-chlorresorcinol | 0.13 | — | — | — | — | — |
| 2-methylresorcinol | — | — | 0.04 | — | — | — |
| m-aminophenol | 0.10 | — | 0.02 | — | 0.27 | 0.465 |
| 1-methoxy-2-amino-4-(2-hydroxyethylamino) benzene | — | 0.21 | — | 0.004 | — | — |
| 6-hydroxyindole | — | 0.18 | — | — | — | — |
| 2,7-napthalenediol | | | 0.01 | — | — | — |
| 2-chloro-6-methyl-3-aminophenol | — | — | — | — | — | 0.014 |
| Isatin | — | 0.06 | — | 0.77 | — | 2.476 |

without RES = without use of resorcinol derivatives

| Coloration with ready-to-use dyeing agent F + OX | F1 | F2 without RES | F3 | F4 without RES | F5 | F6 without RES |
|---|---|---|---|---|---|---|
| L | 23.72 | 23.88 | 43.59 | 43.64 | 14.46 | 14.58 |
| a | 5.84 | 7.32 | 4.50 | 5.57 | 3.79 | 3.80 |
| b | 6.49 | 6.48 | 11.46 | 11.46 | 1.74 | 1.70 |
| Shade | light brown | light brown | medium blond | medium blond | dark brown | dark brown |

| Mixture OFV | F7 | F8 without RES | F9 | F10 without RES | F11 | F12 without RES |
|---|---|---|---|---|---|---|
| p-toluylene diamine (sulfate) | 1.20 | 1.04 | 0.589 | 0.536 | 0.130 | 0.130 |
| 4-amino-3-methylphenol | 0.30 | 0.30 | — | — | 0.380 | 0.54 |

TABLE 3-continued

| (all figures in wt %, relative to the total weight of the color cream) | | | | | | |
|---|---|---|---|---|---|---|
| Resorcinol | 0.07 | — | 0.173 | — | 0.045 | — |
| 4-chlorresorcinol | — | — | 0.045 | — | — | — |
| 2-methylresorcinol | 0.20 | — | 0.046 | — | — | — |
| m-aminophenol | 0.13 | 0.155 | 0.20 | — | — | — |
| 5-amino-2-methylphenol | 0.32 | 0.32 | — | 0.142 | 0.18 | 0.235 |
| 1-naphthol | — | — | — | — | 0.05 | — |
| 2-amino-3-hydroxy-pyridine | 0.20 | 0.24 | 0.025 | — | 0.16 | 0.1330 |
| 4-amino-3-nitrophenol | 0.33 | 0.39 | — | — | — | — |
| 2-amino-6-chloro-4-nitrophenol | — | — | 0.02 | 0.07 | 0.36 | 0.33 |
| Isatin | — | 0.14 | — | 0.189 | — | 0.225 |
| Coloration with ready-to-use dyeing agent F + OX | F7 | F8 without RES | F9 | F10 without RES | F11 | F12 without RES |
| L | 15.05 | 15.09 | 25.08 | 25.06 | 31.03 | 31.01 |
| a | 11.00 | 11.00 | 7.65 | 11.03 | 24.80 | 11.00 |
| b | 3.59 | 3.56 | 3.27 | 3.91 | 27.30 | 27.31 |
| Shade | natural light brown-red | natural light brown-red | light brown gold | light brown gold | dark blond copper | dark blond copper |

The ready-to-use dyes that were obtained using the color creams F2, F4, and F6 dyed the hair in very intense, natural shades in the range of dark brown, medium brown, and dark blond. The shade effect of these colorations showed an almost exact color match with the resorcinol-containing dyes known from the prior art based upon the color creams F1, F3, and F5.

Shades in the natural tone range with a reddish color effect could also be obtained by using dyes according to the invention using the color creams F8, F10, and F12. The shades in the red-blond and copper-blond range corresponded very well in terms of color to the resorcinol-containing dyes known from the prior art based upon the color creams F7, F9, and F11.

3. Other Colorations

For further colorations, the base formulation described in Table 1 was prepared for the color cream. The mixtures of oxidation dye precursors described in Table 4 were each incorporated into the color cream. Each of the color creams produced in this way was mixed in a quantitative ratio of 1:1 with the oxidizing agent preparation OX. Each of the ready-to-use dyeing agents thus produced was then applied to a hair strand (Kerling, natural white) and left there for a period of 30 minutes. The application mixture was then rinsed out with a shampoo and dried. Thereafter, the hair strands were colorimetrically measured (measurement of the lab values).

TABLE 4

| (all figures in wt %, relative to the total weight of the color cream) | | | | | | |
|---|---|---|---|---|---|---|
| Mixture OFV | F13 | F14 | F15 | F16 | F17 | F18 |
| p-toluylene diamine sulfate | 0.016 | — | — | — | — | — |
| N,N-bis(2-hydroxyethyl)-p-phenylene diamine sulfate | — | 0.55 | 0.94 | — | — | — |
| 4-amino-3-methylphenol | — | — | — | 0.3000 | — | 0.53 |
| 2-methoxymethyl-p-phenylene diamine | 1.39 | 0.495 | 1.8000 | 1.3480 | 0.79 | 0.19 |
| m-aminophenol | 0.103 | — | 0.4540 | 0.3000 | — | — |
| 5-amino-2-methylphenol | — | — | — | 0.3200 | 0.38 | 0.297 |
| 6-hydroxyindole | 0.139 | — | — | — | — | — |
| Isatin | 1.067 | 0.75 | 1.60 | 0.10 | 0.306 | 0.228 |
| 2-amino-3-hydroxypyridine | — | — | — | 0.62 | — | 0.138 |
| 2-amino-6-chloro-4-nitrophenol | — | — | — | — | 0.0500 | 0.30 |
| Coloration with ready-to-use dyeing agent F + OX | F13 | F14 | F15 | F16 | F17 | F18 |
| L | 23.76 | 42.74 | 18.40 | 15.17 | 25.18 | 31.00 |
| a | 5.84 | 2.70 | 3.79 | 11.01 | 11.00 | 11.00 |
| b | 6.51 | 8.52 | 1.20 | 3.56 | 3.88 | 27.31 |
| Shade | light brown | medium blond | dark brown | natural light brown-red | light brown gold | dark blond copper |

TABLE 4-continued (all figures in wt %, relative to the total weight of the color cream)

| Mixture OFV | F19 | F20 | F21 | F22 | F23 | F24 |
|---|---|---|---|---|---|---|
| p-toluylene diamine sulfate | — | — | 1.9200 | — | — | — |
| 4-amino-3-methylphenol | — | — | — | — | — | 0.30 |
| 2-(2-hydroxyethyl)-p-phenylene diamine | — | 2.2900 | — | 1.985 | 0.77 | 1.50 |
| 1-hydroxyethyl 4,5-diamino pyrazole sulfate | 0.0004 | 0.0004 | 0.005 | — | — | — |
| 2-methoxymethyl-p-phenylene diamine | 2.30 | — | — | — | — | — |
| m-aminophenol | 0.187 | 0.08 | 0.079 | — | — | 0.068 |
| 5-amino-2-methylphenol | 0.25 | 0.1080 | 0.029 | — | 0.22 | 0.32 |
| 1-methoxy-2-amino-4-(2-hydroxyethylamino)benzene | — | — | — | 0.1550 | — | — |
| 6-hydroxyindole | — | — | — | 0.2830 | — | — |
| Isatin | 0.675 | 0.59 | 0.625 | 0.7740 | 0.1900 | 0.10 |
| 2-amino-3-hydroxypyridine | 0.54 | 0.391 | 0.389 | — | — | 0.54 |
| 4-amino-3-nitrophenol | | 0.0033 | 0.003 | — | 0.06 | — |

| Coloration with ready-to-use dyeing agent F + OX | F19 | F20 | F21 | F22 | F23 | F24 |
|---|---|---|---|---|---|---|
| L | 15.06 | 15.08 | 15.04 | 23.80 | 25.06 | 15.41 |
| a | 11.00 | 11.00 | 11.00 | 5.97 | 11.00 | 10.99 |
| b | 3.59 | 3.60 | 3.60 | 6.47 | 3.80 | 3.56 |
| Shade | natural light brown-red | natural light brown-red | natural light brown-red | light brown | light brown gold | natural light brown-red |

What is claimed is:

1. A multi-component packaging unit for oxidatively dyeing keratinous fibers, the multi-component packaging unit comprising:

a first container containing a dyeing agent, the dyeing agent comprising:

at least one oxidation dye precursor of the developer type selected from the group consisting of p-toluylene diamine, 2-methoxymethyl-p-phenylene diamine, 2-(2-hydroxy-ethyl)-p-phenylene diamine, N,N-bis-(2-hydroxyethyl)-p-phenylene diamine, p-phenylene diamine, 4-amino-3-methylphenol, p-aminophenol, 4,5-diamino-1-(2-hydroxyethyl) pyrazole, and physiologically tolerated salts thereof, isatin, at least one alkalizing agent selected from the group consisting of ammonia, monoethanolamine, 2-amino-2-methylpropanol, arginine, lysine, ornithine, and histidine, and at least one oxidation dye precursor of the coupler type selected from the group consisting of 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylene diamine, 2-(2,4-diaminophenoxy) ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethyl)-1-methylbenzene, 1-amino-3-bis(2-hydroxyethyl) aminobenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, any physiologically tolerated salt thereof, and any mixture thereof; and a second container containing an oxidizing agent composition, the oxidizing agent composition comprising:

at least one oxidizing agent from the group consisting of hydrogen peroxide and its addition products to organic or inorganic compounds, wherein the first container and the second container are packaged separately from one another.

2. The multi-component packaging unit of claim 1, wherein the at least one oxidation dye precursor of the developer type is present in an amount, based on the total weight of the dyeing agent, ranging from 0.001 to 10.0 wt %.

3. The multi-component packaging unit of claim 2, wherein the at least one oxidation dye precursor of the developer type is present in an amount, based on the total weight of the dyeing agent, ranging from 0.1 to 5.0 wt %.

4. The multi-component packaging unit of claim 1, wherein the isatin is present in an amount, based on the total weight of the dyeing agent, ranging from 0.001 to 10 wt %.

5. The multi-component packaging unit of claim 4, wherein the isatin is present in an amount, based on the total weight of the dyeing agent, ranging from 0.15 to 2.5 wt %.

6. The multi-component packaging unit of claim 1, wherein a weight ratio of the at least one oxidation dye precursor of the developer type to the isatin ranges from 2:1 to 1:2.

7. The multi-component packaging unit of claim 6, wherein a weight ratio of the at least one oxidation dye precursor of the developer type to the isatin ranges from 1.8:1 to 1.1:1.

8. The multi-component packaging unit of claim 1, wherein the at least one alkalizing agent is selected from the group consisting of ammonia and monoethanolamine.

9. The multi-component packaging unit of claim 1, wherein the first container further comprises water, and wherein the dyeing agent has a pH ranging from 6.5 to 11.5.

10. The multi-component packaging unit of claim 9, wherein the dyeing agent has a pH ranging from 8.5 to 11.

11. The multi-component packaging unit of claim 1, wherein the at least one oxidation dye precursor of the coupler type is present in an amount, based on the total weight of the dyeing agent, ranging from 0.001 to 10 wt %.

12. The multi-component packaging unit of claim 11, wherein the at least one oxidation dye precursor of the coupler type is present in an amount, based on the total weight of the dyeing agent, ranging from 0.1 to 3.5 wt %.

13. The multi-component packaging unit of claim 1, wherein the dyeing agent further comprises at least one resorcinol-type coupler present in an amount, based on the total weight of the dyeing agent, below 0.1 wt %.

14. The multi-component packaging unit of claim 1, wherein the dyeing agent further comprises at least one surfactant selected from the group consisting of anionic surfactants, amphoteric surfactants, zwitterionic surfactants, and non-ionic surfactants.

15. The multi-component packaging unit of claim 1, wherein the dyeing agent comprises less than 25 wt % of fatty components, based on the total weight of the dyeing agent.

* * * * *